United States Patent
Kizaki et al.

(10) Patent No.: US 6,645,746 B1
(45) Date of Patent: Nov. 11, 2003

(54) CARBONYL REDUCTASE, GENE THEREOF AND METHOD OF USING THE SAME

(75) Inventors: Noriyuki Kizaki, Moriguchi (JP); Yukio Yamada, Kakogawa (JP); Yoshihiko Yasohara, Himeji (JP); Junzo Hasegawa, Akashi (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/890,821

(22) PCT Filed: Nov. 24, 2000

(86) PCT No.: PCT/JP00/08321

§ 371 (c)(1),
(2), (4) Date: Nov. 19, 2001

(87) PCT Pub. No.: WO01/40450

PCT Pub. Date: Jun. 7, 2001

(30) Foreign Application Priority Data

Dec. 3, 1999 (JP) ............................................. 11-345541

(51) Int. Cl.⁷ ............................. C12N 9/02; C12N 1/20; C12N 15/00; C12P 7/42; C07H 21/02
(52) U.S. Cl. .................. 435/189; 435/146; 435/252.33; 435/320.1; 435/255.4; 536/23.2
(58) Field of Search ........................... 435/189, 252.33, 435/320.1, 146, 255.4; 536/23.2

(56) References Cited

U.S. PATENT DOCUMENTS 5,278,313 A   1/1994   Thottathil et al. ............ 548/252

FOREIGN PATENT DOCUMENTS

| WO | 97/00968 | 1/1997 |
| WO | 99/57109 | 11/1999 |
| WO | 00/08011 | 2/2000 |
| WO | 00/36134 | 6/2000 |
| WO | 01/04336 | 1/2001 |

OTHER PUBLICATIONS

Shimizu S. et al. Chiral alcohol synthesis with yeast carbonyl reductases, J. Mol. Catalysis B: Enzymatic, 1998, 5, 321–325.*
Shimizu S. et al. Chiral alcohol synthesis with microbial carbonyl reductases in a water–organic solvent two–phase system, Annals of the New York Academy of Sciences, 1998, 864, 87–95.*
Yasohara Y. Molecular cloning and overexpression of the gene encoding an NADPH–dependent carbonyl reductase from *Candidia magnoliae*, involved in stereoselective reduction of ethyl 4–chloro–3–oxobutanoate, Biosci. Biotechnol. Biochem, 2000, 64, 1430–1436.1.*
M. Wada, et al., "Purification and Characterization of NADPH–Dependent Carbonyl Reductase, Involved in Stereoselective Reduction of Ethyl 4–Choloro–3–oxobutanoate, from *Candida magnoliae*", Biosci. Biotechnol. Biochem., 62(2):280–285 (1998).

* cited by examiner

Primary Examiner—Ponnathapu Achutamurthy
Assistant Examiner—Malgorzata Walicka
(74) Attorney, Agent, or Firm—Kenyon & Kenyon (57) ABSTRACT

A novel polypeptide for producing tert-butyl (3R,5S)-6-chloro-3,5-dihydroxyhexanoate, a gene encoding the polypeptide, and a method of using the polypeptide, are provided. The polypeptide has an enzyme activity to asymmetrically reduce tert-butyl (S)-6-chloro-5-hydroxy-3-oxohexanoate to tert-butyl (3R,5S)-6-chloro-3,5-dihydroxyhexanoate. The polypeptide comprises the amino acid sequence represented by SEQ ID NO. 1 in the Sequence Listing, or the amino acid sequence having at least one amino acid substitution, insertion, deletion, or addition thereof.

15 Claims, 2 Drawing Sheets

```
         10        20        30        40        50        60
GCATGCACGCTACGAAGTGTGCTTACAGATGTCACGTAAGTGTGCATGTGCGTTGCGTGT 70        80        90       100       110       120
GCGTTGCGTGTGTGTTGTGGGAATATAAAAGGGCGCAGTTGACTTGACTCGAGACTGTGC 130       140       150       160       170       180
ACTAACCTACACCAAAGCTACAAAGATGTCGACTCCGTTGAATGCTCTCGTAACTGGCGC
                            M  S  T  P  L  N  A  L  V  T  G  A 190       200       210       220       230       240
TAGCCGCGGCATTGGCGCTGCTACTGCCATTAAGCTCGCCGAGAATGGATACAGTGTGAC
 S  R  G  I  G  A  A  T  A  I  K  L  A  E  N  G  Y  S  V  T 250       260       270       280       290       300
GCTGGCTGCGCGTAATGTCGCGAAGCTGAACGAAGTGAAGGAGAAGCTGCCTGTGGTCAA
 L  A  A  R  N  V  A  K  L  N  E  V  K  E  K  L  P  V  V  K 310       320       330       340       350       360
GGACGGCCAGAAGCACCACATCTGGGAGCTCGATCTTGCGAGCGTTGAGGCTGCATCGTC
 D  G  Q  K  H  H  I  W  E  L  D  L  A  S  V  E  A  A  S  S 370       380       390       400       410       420
CTTCAAGGGCGCGCCTTTACCGGCTAGCGACTACGATCTGTTCGTTTCGAATGCTGGCAT
 F  K  G  A  P  L  P  A  S  D  Y  D  L  F  V  S  N  A  G  I 430       440       450       460       470       480
TGCGCAGTTCACGCCAACGGCGGACCAAACCGACAAGGACTTCCTGAACATTCTCACCGT
 A  Q  F  T  P  T  A  D  Q  T  D  K  D  F  L  N  I  L  T  V 490       500       510       520       530       540
GAACCTCTCCTCCCCCATTGCGCTCACGAAGGCCCTACTGAAGGGCGTCTCCGAGAGGTC
 N  L  S  S  P  I  A  L  T  K  A  L  L  K  G  V  S  E  R  S 550       560       570       580       590       600
GAACGAGAAGCCGTTCCATATTATCTTCCTCTCGTCCGCTGCAGCCCTGCACGGAGTCCC
 N  E  K  P  F  H  I  I  F  L  S  S  A  A  A  L  H  G  V  P 610       620       630       640       650       660
TCAGACTGCAGTCTACAGTGCTTCGAAGGCGGGGCTTGACGGTTTCGTGCGCTCTCTTGC
 Q  T  A  V  Y  S  A  S  K  A  G  L  D  G  F  V  R  S  L  A 670       680       690       700       710       720
TCGCGAGGTGGGTCCGAAGGGCATTCATGTGAACGTTATTCATCCTGGTTGGACGAAGAC
 R  E  V  G  P  K  G  I  H  V  N  V  I  H  P  G  W  T  K  T 730       740       750       760       770       780
TGACATGACGGATGGTATTGACGACCCCAATGATACTCCTATCAAGGGCTGGATCCAGCC
 D  M  T  D  G  I  D  D  P  N  D  T  P  I  K  G  W  I  Q  P 790       800       810       820       830       840
TGAGGCGATTGCTGATGCGGTTGTGTTCCTGGCAAAGTCGAAGAACATCACAGGCACTAA
 E  A  I  A  D  A  V  V  F  L  A  K  S  K  N  I  T  G  T  N 850       860       870       880       890       900
TATCGTGGTGGACAATGGCTTGCTCGCTTGAGTAGATAGAACGGTTTTACGCAATGTTGT
 I  V  V  D  N  G  L  L  A  *

910       920       930       940       950       960
TATTACACTTATCGGCAAGGAAACTGCTTTTATGGAGCATGGCCTAGTGTATTGAAACTC 970       980       990      1000       1010
CAAAAATTAATTAGAGCATACAACACATGGCACCACCGAATTC
```

CARBONYL REDUCTASE, GENE THEREOF AND METHOD OF USING THE SAME

This application claims benefits of the International Application PCT/JP00/08321 filed Nov. 24, 2000, and the Japanese Patent Application 11345541 filed Dec. 3, 1999.

TECHNICAL FIELD

The present invention relates to a novel polypeptide, a gene encoding the polypeptide, an expression vector for expressing the polypeptide, a transformant obtained by transforming a host cell using the expression vector, and a method for producing a compound useful as a material for synthesis of medicaments and pesticides using the transformant. More particularly, the present invention relates to a polypeptide isolated from a microorganism having an enzyme activity to asymmetrically reduce tert-butyl (S)-6-chloro-5-hydroxy-3-oxohexanoate to tert-butyl (3R,5S)-6-chloro-3,5-dihydroxyhexanoate, a polynucleotide encoding the polypeptide, an expression vector including the polynucleotide, and a transformant transformed by the expression vector.

The present invention also relates to a method for producing tert-butyl (3R,5S)-6-chloro-3,5-dihydroxyhexanoate. The method includes the steps of reacting the transformant or a processed product thereof with tert-butyl (S)-6-chloro-5-hydroxy-3-oxohexanoate, and collecting the produced tert-butyl (3R,5S)-6-chloro-3,5-dihydroxyhexanoate.

Tert-butyl (3R,5S)-6-chloro-3,5-dihydroxyhexanoate is a compound useful as a material for synthesis of medicaments and pesticides, particularly HMG-CoA reductase inhibitors.

BACKGROUND ART

The only method for producing tert-butyl (3R,5S)-6-chloro-3,5-dihydroxyhexanoate by asymmetrically reducing tert-butyl (S)-6-chloro-5-hydroxy-3-oxohexanoate, which has been reported, employs diethylmethoxyborane and sodium borohydride (U.S. Pat. No. 5,278,313). Problems with this technique are that a very low temperature reaction vessel achieving temperatures as low as −78° C. is required, that expensive materials need to be employed, and the like. There has been a demand for a practical reaction procedure.

DISCLOSURE OF THE INVENTION

The inventors of the present invention found a polypeptide derived from a microorganism which asymmetrically reduces tert-butyl (S)-6-chloro-5-hydroxy-3-oxohexanoate to produce tert-butyl (3R,5S)-6-chloro-3,5-dihydroxyhexanoate, envisioned a method which can efficiently produce tert-butyl (3R,5S)-6-chloro-3,5-dihydroxyhexanoate, and eventually achieved the present invention.

An objective of the present invention is to provide a polypeptide capable of asymmetrically reducing tert-butyl (S)-6-chloro-5-hydroxy-3-oxohexanoate to produce tert-butyl (3R,5S)-6-chloro-3,5-dihydroxyhexanoate. Another objective of the present invention is to provide a method for efficiently producing the polypeptide using recombinant DNA technology. Still another objective of the present invention is to provide a transformant which can produce said polypeptide, and a polypeptide having a glucose dehydrogenase activity, simultaneously to a large extent. Even still another objective of the present invention is to provide a practical method for producing tert-butyl (3R,5S)-6-chloro-3,5-dihydroxyhexanoate using the transformant.

The present invention relates to a polypeptide having an enzyme activity to asymmetrically reduce tert-butyl (S)-6-chloro-5-hydroxy-3-oxohexanoate to tert-butyl (3R,5S)-6-chloro-3,5-dihydroxyhexanoate. The polypeptide comprises the amino acid sequence represented by SEQ ID NO. 1 in the Sequence Listing, or the amino acid sequence having at least one amino acid substitution, insertion, deletion, or addition thereof.

Preferably, the peptide may be derived from a microorganism belonging to genus Candida. More preferably, the microorganism may be *Candida magnoliae* IFO 0705.

In one aspect, the present invention relates to a polynucleotide encoding the above-described polypeptide.

In one aspect, the present invention relates to a polynucleotide encoding a polypeptide having an enzyme activity to asymmetrically reduce tert-butyl (S)-6-chloro-5-hydroxy-3-oxohexanoate to tert-butyl (3R,5S)-6-chloro-3,5-dihydroxyhexanoate. The polynucleotide is hybridized with a nucleotide sequence represented by SEQ ID NO. 2 in the Sequence Listing under stringent conditions.

In one aspect, the present invention relates to an expression vector including the above-described polynucleotide. Preferably, the expression vector may be plasmid pNTCR.

In one embodiment, the above-described expression vector may further include a polynucleotide encoding a polypeptide having a glucose dehydrogenase activity.

Preferably, the polypeptide having a glucose dehydrogenase activity may be a glucose dehydrogenase derived from *Bacillus megaterium*.

Preferably, the expression vector may be plasmid pNTCRG.

In one aspect, the present invention relates to a transformant obtained by transforming a host cell using the above-described expression vector.

Preferably, the host cell may be *Escherichia coli*. More preferably, the transformant may be *E. coli* HB101 (pNTCR) or *E. coli* HB101 (pNTCRG).

In one aspect, the present invention relates to a method for producing tert-butyl (3R,5S)-6-chloro-3,5-dihydroxyhexanoate. The method comprises the steps of reacting the above-described transformant and/or a processed product thereof with tert-butyl (S)-6-chloro-5-hydroxy-3-oxohexanoate, and collecting produced tert-butyl (3R,5S)-6-chloro-3,5-dihydroxyhexanoate.

Preferably, the reacting step is carried out in the presence of a coenzyme restoring system.

DESCRIPTION OF THE DRAWINGS

FIG. 1 is a diagram showing the sequence of a polynucleotide (SEQ ID NO: 9) of the present invention, and the predicted amino acid sequence (SEQ ID NO: 1) thereof

BEST MODE FOR CARRYING OUT THE INVENTION

Hereinafter, the present invention will be described in detail. As a polypeptide of the present invention, any polypeptide may be employed as long as it has an enzyme activity to asymmetrically reduce tert-butyl (S)-6-chloro-5-hydroxy-3-oxohexanoate represented by the following formula (I) to produce tert-butyl (3R,5S)-6-chloro-3,5- dihydroxyhexanoate represented by the following formula (II).

tert-butyl (S)-6-chloro-5-hydroxy-3-oxohexanoate tert-butyl (3R,5S)-6-chloro-3,5-dihydroxyhexanoate Examples of such polypeptides include a polypeptide comprising the amino acid sequence of SEQ ID NO. 1 in the Sequence Listing and a polypeptide comprising an amino acid sequence having at least one amino acid substitution, insertion, deletion, or addition, or a part thereof, and having an enzyme activity to asymmetrically reduce tert-butyl (S)-6-chloro-5-hydroxy-3-oxohexanoate to produce tert-butyl (3R,5S)-6-chloro-3,5-dihydroxyhexanoate.

A polypeptide of the present invention can be obtained from a microorganism having an activity to asymmetrically reduce tert-butyl (S)-6-chloro-5-hydroxy-3-oxohexanoate to produce tert-butyl (3R,5S)-6-chloro-3,5-dihydroxyhexanoate. Therefore, the microorganism used as a source of the polypeptide may be, not limited to, yeast (genus Candida), and most preferably *Candida magnoliae* IFO 0705. This strain was a microorganism deposited originally under the deposit number CBS166 at Centraalbureau voor Schimmelcultures (CBS; Oosterstraat 1, Postbus 273, NL-3740 AG Baarn, Netherlands), and the isolation and properties of the strain are described in "The Yeasts, a Taxonomic Study. 3rd ed. pp. 731 (1984)". Microorganisms producing polypeptides of the present invention may be of a wild type or variant type strain. Alternatively, microorganisms genetically engineered (using cell fusion, gene manipulation, etc.) may be employed. Microorganisms genetically engineered to produce peptides of the present invention can be obtained by a method including the steps of: isolating and/or purifying these enzymes and determining the entire or partial amino acid sequence thereof; determining nucleotide sequences encoding the polypeptides based on the amino acid sequences thereof; obtaining nucleotide sequences encoding the polypeptides based on the amino acid sequences thereof; introducing the nucleotide sequences into other microorganisms to obtain recombinant microorganisms; and cultivating the recombinant microorganisms to obtain enzymes of the present invention.

A culture medium for microorganisms producing polypeptides of the present invention may be any liquid nutrient medium containing a typical carbon source, nitrogen source, mineral salt source, organic nutrient source, and the like as long as the microorganisms can grow.

The term "microorganism culture" as used herein refers to a microorganism itself or a liquid culture containing the microorganism, and "its processed product" refers to a product obtained by extraction or purification of the microorganism itself or the liquid culture containing the microorganism.

Polypeptides of the present invention can be purified from microorganisms containing the polypeptides using a conventional method. For example, a microorganism is cultivated in an appropriate medium, and the culture is centrifuged to harvest the microorganism. The microorganism is disrupted by Dyno mill (manufactured by Willy A. Bachofen Co., Ltd.), for example, and centrifuged to remove cell debris and thus obtain a cell-free extract. The cell-free extract is then subjected to techniques, such as salting-out (e.g., ammonium sulfate precipitation and sodium phosphate precipitation), solvent precipitation (a protein fractionation precipitation method using acetone, ethanol, or the like), dialysis, gel filtration, ion exchange, column chromatography (e.g., reverse phase chromatography), and ultrafiltration, alone or in combination, to purify the polypeptides. Enzyme activity can be determined by measuring the reduction in absorption at a wavelength of 340 nm at 30° C. where 5 mM tert-butyl (S)-6-chloro-5-hydroxy-3-oxohexanoate as a substrate, 0.33 mM NADPH as a coenzyme, and an enzyme are added to a 100 mM phosphate buffer (pH 6.5).

Polypeptides of the present invention may include the amino acid sequence of SEQ ID NO. 1 in the Sequence Listing. Polypeptides having an amino acid sequence having at least one amino acid substitution, insertion, deletion, or addition, or apart thereof, and having an enzyme activity to asymmetrically reduce tert-butyl (S)-6-chloro-5-hydroxy-3-oxohexanoate to produce tert-butyl (3R,5S)-6-chloro-3,5-dihydroxyhexanoate can be prepared from a polypeptide having the amino acid sequence of SEQ ID NO. 1 in the Sequence Listing using a known method described in Current Protocols in Molecular Biology (John Wiley and Sons, Inc., 1989), or the like. Any polypeptide falls within the scope of the present invention as long as it has the enzyme activity to asymmetrically reduce tert-butyl (S)-6-chloro-5-hydroxy-3-oxohexanoate to tert-butyl (3R,5S)-6-chloro-3,5-dihydroxyhexanoate.

Polynucleotides of the present invention may be any polynucleotide encoding any one of the above-described polypeptides. An example of a polynucleotide of the present invention is a polynucleotide having the nucleotide sequence of SEQ ID NO. 2 in the Sequence Listing, and a polynucleotide capable of being hybridized with that polynucleotide under stringent conditions.

The polynucleotide capable of being hybridized with the polynucleotide having the nucleotide sequence of SEQ ID NO. 2 in the Sequence Listing under stringent conditions means a polynucleotide obtained with a colony hybridization method, a plaque hybridization method, a southern hybridization method or the like when the nucleotide sequence of SEQ ID No.2 is used as a DNA probe. Specifically, the polynucleotide can be identified as follows. A filter on which polynucleotides derived from a colony or plaque are immobilized is subjected to hybridization with the nucleotide sequence of SEQ ID No.2 in 0.7 to 1.0 M NaCl at 65° C., and thereafter the filter is washed with an SSC solution having 0.1 to 2-fold concentration (one-fold concentration SSC solution contains 150 mM sodium chloride and 15 mM sodium citrate) at 65° C.

Hybridization may be carried out in accordance with a procedure described in Molecular Cloning, A laboratory manual, second edition (Cold Spring Harbor Laboratory Press, 1989), or the like. Specifically, examples of a polynucleotide capable of the above-described hybridization include a polynucleotide having at least 60% sequence identity with the nucleotide sequence of SEQ ID NO. 2, preferably at least 80% sequence identity, more preferably at least 90% sequence identity, even more preferably at least 95% sequence identity, and most preferably at least 99% sequence identity.

Polynucleotides of the present invention encoding polypeptides having the enzyme activity to asymmetrically reduce tert-butyl (S)-6-chloro-5-hydroxy-3-oxohexanoate to tert-butyl (3R,5S)-6-chloro-3,5-dihydroxyhexanoate include a polynucleotide having at least 60% sequence identity with the nucleotide sequence of SEQ ID NO. 2, preferably at least 80% sequence identity, more preferably at least 90% sequence identity, even more preferably at least 95% sequence identity, and most preferably at least 99% sequence identity, as long as the encoded polypeptides have the above-described enzyme activity. The term "sequence identity" means that two polynucleotide sequences to be compared are identical to each other, and the rate (%) of sequence identity between two polynucleotides to be compared is calculated as follows. First, two polynucleotide sequences to be compared are aligned in an optimal manner. The number of sites at which the same nucleic-acid base (e.g., A,T,C,G,U, or I) is present on both sequences (the number of matched sites) is counted and the number of matched sites is divided by the total number of nucleic-acid bases in the polynucleotide. The resultant value is multiplied by 100. Sequence identity can be calculated using the following sequence analyzing tool, for example: Unix-based GCG Wisconsin Package (Program Manual for the Wisconsin Package, Version 8, September, 1994, Genetics Computer Group, 575 Science Drive Madison, Wis., USA53711; Rice P. (1996) Program Manual for EGCG Package, Peter Rice, The Sanger Centre, Hinxton Hall, Cambridge, CB10 1RQ, England) and the ExPASy World Wide Web server for molecular biology (Geneva University Hospital and University of Geneva, Geneva, Switzerland).

Polynucleotides of the present invention can be obtained from microorganisms having the enzyme activity to asymmetrically reduce tert-butyl (S)-6-chloro-5-hydroxy-3-oxohexanoate to tert-butyl (3R,5S)-6-chloro-3,5-dihydroxyhexanoate. The microorganism used as a source of the polynucleotide may be, not limited to, yeast (genus Candida), and most preferably *Candida magnoliae* IFO 0705.

Hereinafter, a method for producing a polynucleotide of the present invention from microorganisms having the enzyme activity to asymmetrically reduce tert-butyl (S)-6-chloro-5-hydroxy-3-oxohexanoate to tert-butyl (3R,5S)-6-chloro-3,5-dihydroxyhexanoate will be described. The present invention is not limited to this.

Initially, the amino acid sequences of the purified polypeptide, and peptide fragments obtained by digesting the polypeptide with an appropriate endopeptidase are sequenced by the Edman method. Based on this amino acid sequence information, a nucleotide primer is synthesized. Thereafter, chromosomal DNA is prepared from a microorganism, from which the polynucleotide is originated, using a typical nucleotide isolation method (e.g., Hereford method described in Cell, 18, 1261 (1979)). PCR is carried out using the above-described nucleotide primer and this chromosomal DNA as a template to amplify a part of the polypeptide gene. Further, the amplified part of the polypeptide gene is labeled with a random primer labeling method described in Anal. Biochem., 132, 6 (1983), for example, to prepare a nucleotide probe. The chromosomal DNA of the microorganism is digested by an appropriate restriction enzyme. The resultant fragments are incorporated into a vector which is in turn introduced into an appropriate host cell, thereby constructing a DNA library of chromosomal DNA of the microorganism. This DNA library is screened using the above-described nucleotide probe in accordance with a colony hybridization method, a plaque hybridization method, or the like, thereby obtaining DNA including the polypeptide gene. The nucleotide sequence of the thus-obtained DNA fragment including the polypeptide gene can be sequenced with a dideoxy sequencing method, a dideoxy chain termination method, or the like. For example, the sequencing of the nucleotide sequence may be carried out using ABI PRISM Dye Terminator Cycle Sequencing Ready Reaction Kit (manufactured by Perkin Elmer Co., Ltd.) and ABI 373A DNA Seqencer (manufactured by Perkin Elmer Co., Ltd.).

Vectors for introducing polynucleotides of the present invention into host microorganisms, in which the polynucleotides are expressed, may be any vector as long as the enzyme gene can be expressed in the appropriate host microorganisms. Examples of such vectors include a plasmid vector, a phage vector, and a cosmid vector. A shuttle vector may be used that can exchange a gene between host strains. Such a vector typically includes a control element, such as a lacUV5 promoter, a trp promoter, a trc promoter, a tac promoter, a lpp promoter, a tufB promoter, a recA promoter, or a pL promoter, and is preferably employed as an expression vector including an expression unit operatively linked to the polynucleotide of the present invention.

The term "control element" as used herein refers to a functional promoter and a nucleotide sequence having any associated transcription element (e.g., enhancer, CCAAT box, TATA box, SPI site).

The phrase "operatively linked" as used herein refers to that a polynucleotide is linked with controlling elements, such as a promoter and an enhancer, which control expression of the polynucleotide in such a manner that the controlling elements can operate to express the gene. It is well known to those skilled in the art that the types of control elements may vary depending on the host cell.

Examples of host cells, into which a vector having a polynucleotide of the present invention is introduced, include bacteria, yeast, molds, plant cells, and animal cells. *Escherichia coli* is particularly preferable. A polynucleotide of the present invention can be introduced into a host cell using a conventional method. When *E. coli* is used as a host cell, a polynucleotide of the present invention can be introduced using a calcium chloride method, for example.

When producing tert-butyl (3R,5S)-6-chloro-3,5-dihydroxyhexanoate by asymmetrically reducing tert-butyl (S)-6-chloro-5-hydroxy-3-oxohexanoate using a polypeptide of the present invention, a coenzyme, such as NADPH and NADH, is required. However, an enzyme capable of transforming an oxidized coenzyme to a reduced coenzyme (hereinafter referred to as coenzyme restoring capability) can be used along with a corresponding substrate, i.e., a coenzyme restoring system is used in combination with a polypeptide of the present invention in reaction, thereby reducing the quantity of expensive coenzyme used. Examples of enzymes having coenzyme restoring capability include hydrogenase, formate dehydrogenase, alcohol dehydrogenase, aldehyde dehydrogenase, glucose-6-phosphate dehydrogenase, and glucose dehydrogenase. Preferably, glucose dehydrogenase is used. Such a reaction may be carried out by adding a coenzyme restoring system to an asymmetric reaction system. When using, as a catalyst, a transformant transformed both with a polynucleotide encoding a polypeptide having the enzyme activity to asymmetrically reduce tert-butyl (S)-6-chloro-5-hydroxy-3-oxohexanoate to produce tert-butyl (3R,5S)-6-chloro-3,5-dihydroxyhexanoate, and a polynucleotide encoding a polypeptide having a glucose dehydrogenase activity, the reactions can be efficiently carried out without preparing an enzyme having the coenzyme restoring capability and adding the enzyme to a reaction system. Such a transformant can be obtained by incorporating a polynucleotide encoding a polypeptide having the enzyme activity to asymmetrically reduce tert-butyl (S)-6-chloro-5-hydroxy-3-oxohexanoate to produce tert-butyl (3R,5S)-6-chloro-3,5-dihydroxyhexanoate, and a polynucleotide encoding a polypeptide having a glucose dehydrogenase activity, into the same vector, and introducing the vector into a host cell. Alternatively, the transformant can be obtained by incorporating these two polynucleotides into two vectors derived from incompatible groups, and introducing these polynucleotides into the same host cell.

Glucose dehydrogenase activity of the transformant can be determined by measuring an increase in absorption at a wavelength of 340 nm at 25° C. where 0.1 M glucose as a substrate, 2 mM NADP as a coenzyme, and an enzyme are added to a 1 M Tris HCl buffer (pH 8.0).

Production of tert-butyl (3R,5S)-6-chloro-3,5-dihydroxyhexanoate using a transformant of the present invention may be carried out as follows.

Initially, tert-butyl (S)-6-chloro-5-hydroxy-3-oxohexanoate as a substrate, a coenzyme such as NADP, and the culture of the transformant or a processed product thereof are added to an appropriate solvent, followed by pH adjustment. The resultant mixture is stirred to be reacted. The reaction is carried out at a temperature of 10° C. to 70° C. while maintaining the pH of the reaction solution in the range of 4 to 10. The reaction is carried out in a batch process or a continuous process. In the case of a batch process, a substrate to be reacted is added to prepare a concentration of 0.1% to 70% (w/v). The processed product of a transformant and the like mentioned above refers to a crude extract, cultured microorganisms, lyophilized organisms, acetone dried organisms, homogenates of such microorganisms, and the like. Such processed products and the like may be used in the state of being immobilized as enzymes or microorganisms as they are, by a known means. When the reaction is carried out using a transformant which produces a polypeptide of the present invention and a glucose dehydrogenase, addition of glucose to the reaction system allows a reduction in the quantity of coenzymes to a large extent.

Tert-butyl (3R,5S)-6-chloro-3,5-dihydroxyhexanoate produced by the reaction can be purified by a conventional method. For example, tert-butyl (3R,5S)-6-chloro-3,5-dihydroxyhexanoate is subjected to centrifugation, filtration and other processes as required to remove suspending substances such as microorganisms. The resultant product is subjected to extraction with an organic solvent such as ethyl acetate and toluene, and dehydrated with a dehydrant such as sodium sulfate. The organic solvent is removed under decompression. The resultant product is then subjected to crystallization, chromatography, or the like to be purified.

In the reaction, tert-butyl (S)-6-chloro-5-hydroxy-3-oxohexanoate as a substrate is prepared with a method described in U.S. Pat. No. 52,783,131 which is herein incorporated by reference.

Quantification of tert-butyl (S)-6-chloro-5-hydroxy-3-oxohexanoate and tert-butyl (3R,5S)-6-chloro-3,5-dihydroxyhexanoate, and measurement of the diastereomer ratio of tert-butyl (3R,5S)-6-chloro-3,5-dihydroxyhexanoate can be performed by high performance liquid chromatograhy (column: COSMOSIL 5CN-R (ID 4.6×250 mm) manufactured by Nacalai Tesque Co., Ltd., eluant: 1 mM phosphate solution/acetonitrile=5/1, flow rate: 0.7 ml/min, detection: 210 nm, column temperature: 30° C.).

As described above, according to the present invention, it is possible to efficiently produce a polypeptide of the present invention. With such a polypeptide, an excellent method for producing tert-butyl (3R,5S)-6-chloro-3,5-dihydroxyhexanoate can be provided. Hereinafter, the present invention will be described by way of illustrative examples with reference to the accompanying drawings. The present invention is not limited to such examples.

EXAMPLES

The details of manipulation methods relating to recombinant DNA techniques employed in the following examples are described in the following texts.

Molecular Cloning 2nd Edition(Cold Spring Harbor Laboratory Press, 1989)

Current Protocols in Molecular Biology(Greene Publishing Associates and Wiley-Interscience)

Example 1

Purification of a Polypeptide Having Asymmetrical Reduction Enzyme Activity

From *Candida magnoliae* IFO 0705, a polypeptide having the enzyme activity to asymmetrically reduce tert-butyl (S)-6-chloro-5-hydroxy-3-oxohexanoate to tert-butyl (3R,5S)-6-chloro-3,5-dihydroxyhexanoate is purified singly in the following manner.

(Cultivation of *Candida Magnoliae* IFO 0705)

18 l of liquid medium having the following composition was prepared in a 30 l jar fermenter (manufactured by Marubishi Bioeng Co., Ltd.), and sterilized with steam at 120° C. for 20 minutes.

Composition of medium: tap water, glucose 4.0%, yeast extract 0.5%, $KH_2PO_4$ 0.1%, $(NH_4)_2HPO_4$ 0.65%, NaCl 0.1%, $MgSO_4.7H_2O$ 0.8%, $ZnSO_4.7H_2O$ 0.06%, $FeSO_4.7H_2O$ 0.09%, $CuSO_4.5H_2O$ 0.005%, $MnSO_4.4-6H_2O$ 0.01%, and Adecanol™ LG-109 (Manufactured by NOF Corporation) 0.02% (pH 7.0).

The above medium was inoculated with a culture of *Candida magnoliae* IFO 0705, which had been pre-cultured in the medium, by 180 ml/fermenter and cultured at 33° C. with agitation at 295 rpm at an aeration rate of 5.0 NL/min while maintaining the lower limit of pH at 6.5 by dripping 30% (w/w) aqueous sodium hydroxide. 655 g of 55% (w/w) aqueous glucose solution was added 22 hours and 25 hours after the start of the cultivation. The cultivation was carried out for 30 hours.

(Preparation of Cell-free Extract)

Microorganisms were collected from 10 L of the resultant culture by centrifugation and then washed with a physiological saline solution, thereby obtaining 1350 g of wet microorganisms. The wet microorganisms were suspended in 2700 ml of a 100 mM phosphate buffer (pH 6.7), and 2-mercaptoethanol and phenylmethylsulfonyl fluoride were added to final concentrations of 5 mM and 0.1 mM, respectively. The microorganisms were disrupted by Dyno mill (manufactured by Willy A. Bachofen Co., Ltd.). The disrupted microorganisms were centrifuged to remove cell debris, thereby obtaining 2880 ml of a cell-free extract.

(Ammonium Sulfate Fractionation)

Ammonium sulfate was added to and dissolved in the cell-free extract so as to obtain 60% saturation. The resultant precipitates were removed by centrifugation (in this case, the pH of the cell-free extract was maintained at 6.7 with ammonia water). Ammonium sulfate was further added to the supernatant to obtain 75% saturation while maintaining pH 6.7 similarly. The resultant precipitates were collected by centrifugation. The precipitates were dissolved and dialyzed overnight in 10 mM phosphate buffer (pH 7.0) containing 2 mM 2-mercaptoethanol.

(DEAE-TOYOPEARL Column Chromatography)

The above resultant crude enzyme solution was supplied to a DEAE-TOYOPEARL 650M (500ml; manufactured by Tosoh Corporation) column which had been equilibrated with 10 mM phosphate buffer (pH 7.0) containing 2 mM 2-mercaptoethanol, so that polypeptides having enzyme activity were adsorbed to the column. The column was washed with the same buffer. Active fractions were eluted using a linear gradient of NaCl (from 0 M to 0.5 M). The active fractions were collected and then dialyzed overnight in 10 mM phosphate buffer (pH 7.0) containing 2 mM 2-mercaptoethanol.

(Phenyl Sepharose Column Chromatography)

Ammonium sulfate was dissolved in the above resultant crude enzyme solution to a final concentration of 1 M (while maintaining pH 7.0 with ammonia water), and then supplied to a Phenyl sepharose CL-4B column (140 ml; manufactured by Pharmacia Biotech Co., Ltd.) which had been equilibrated with 10 mM phosphate buffer (pH 7.0) containing 2 mM 2-mercaptoethanol and 1 M ammonium sulfate, so that polypeptides having enzyme activity were adsorbed to the column. The column was washed with the same buffer. Active fractions were eluted using a linear gradient of ammonium sulfate (from 1 M to 0 M). The active fractions were collected and then dialyzed overnight in 10 mM phosphate buffer (pH 7.0) containing 2 mM 2-mercaptoethanol.

(Blue Sepharose Column Chromatography)

The above resultant crude enzyme solution was supplied to a Blue sepharose CL-6B column (40 ml; manufactured by Pharmacia Biotech Co., Ltd.) which had been equilibrated with 10 mM phosphate buffer (pH 7.0) containing 2 mM 2-mercaptoethanol, so that polypeptides having enzyme activity were adsorbed to the column. The column was washed with the same buffer. Active fractions were eluted using a linear gradient of NaCl (from 0 M to 1 M). The active fractions were collected and then dialyzed overnight in 10 mM phosphate buffer (pH 7.0) containing 2 mM 2-mercaptoethanol.

(SuperQ-TOYOPEARL Column Chromatography)

The above resultant crude enzyme solution was supplied to a SuperQ-TOYOPEARL 650S column (12 ml; manufactured by Tosoh Corporation) which had been equilibrated with a 10 mM phosphate buffer (pH 7.0) containing 2 mM 2-mercaptoethanol, so that polypeptides having enzyme activity were adsorbed to the column. The column was washed with the same buffer. Active fractions were eluted using a linear gradient of NaCl (from 0 M to 0.4 M). The active fractions were collected and then dialyzed overnight in a 10 mM phosphate buffer (pH 7.0) containing 2 mM 2-mercaptoethanol. Thus, a pure polypeptide specimen which is electrophoretically single was obtained (hereinafter referred to as a CR enzyme).

Example 2

Cloning of CR Enzyme Gene (Preparation of Synthetic Oligonucleotide Probe)

The purified CR enzyme obtained in Example 1 was denatured in the presence of 8 M urea, and then digested with lysyl endopeptidase derived from Achromobacter (manufactured by Wako Pure Chemical Industries, Ltd.). The amino acid sequences of the resultant peptide fragments were determined using ABI492 protein sequencer (manufactured by Perkin Elmer Co., Ltd.). Based on the amino acid sequences, two nucleotide primers (SEQ ID NOs. 3 and 4) were synthesized with a conventional method.

(Amplification of CR Enzyme Gene by PCR)

Chromosomal DNA was extracted from cultured *Candida magnoliae* IFO 0705 in accordance with the Hereford method (Cell, 18, 1261 (1979)). Thereafter, PCR was carried out using the above-prepared nucleotide primer and the resultant chromosomal DNA as a template, thereby amplifying a nucleotide fragment of about 350 bp which is considered to be a part of the CR enzyme gene.

(Preparation of Chromosomal DNA Library)

The chromosomal DNA of *Candida magnoliae* IFO 0705 was completely digested with restriction enzyme ApaI, and the digested fragments were separated with agarose gel electrophoresis. Thereafter, a southern method (J. Mol. Biol., 98, 503 (1975)) was carried out using the 350-bp DNA fragment obtained above to analyze the digested fragments of the chromosomal DNA (the labeling and detection of a nucleotide probe were carried out using Gene Images Labeling and Detection System (manufactured by Amersham Co., Ltd.)). As a result, it was found that a nucleotide fragment of about 5.5 kb was hybridized with the nucleotide probe.

Based on this fact, after the digested fragments were separated by agarose gel electrophoresis, nucleotide fragments of 4.3 kb to 6.2 kb were collected. These nucleotide fragments were introduced into the ApaI site of plasmid vector pBluescriptII KS(−) (manufactured by STRATAGENE Co., Ltd.). The plasmid was introduced into *E. coli* JM109. The chromosomal DNA library of this strain was prepared.

(Screening of Chromosomal DNA Library)

The thus-obtained nucleotide fragment was used as a probe to screen the chromosomal DNA library in accordance with a colony hybridization method (the labeling and detection of a nucleotide probe were carried out using Gene Images Labeling and Detection System (manufactured by Amersham Co., Ltd.), and the experiment was carried out in accordance with procedures described in the instruction manual of the system). As a result, a single positive colony was obtained. Thereafter, recombinant plasmids obtained from the positive colony, into which DNA of about 5.5 kb had been inserted, were double digested with EcoRI and SphI. The digested fragments were analyzed with the southern method as described above. As a result, nucleotide fragments of about 1.0 kb produced by the digestion using the restriction enzymes were hybridized with the probe. Based on this fact, the nucleotide fragment of about 1.0 kb was inserted into the EcoRI-SphI site of plasmid pUC19 (manufactured by Takara Shuzo Co., Ltd.) to construct recombinant plasmid pUC-ES and selected as a chromosomal DNA clone including the CR enzyme gene.

(Determination of Base Sequence)

The above recombinant plasmid pUC-ES was digested with a variety of restriction enzymes, and digested fragments produced during the reaction were analyzed to prepare a restriction map. Then, various DNA fragments obtained during the analysis were Cinserted into multi-cloning sites of pUC19, to construct recombinant plasmids, nucleotide sequences of the respective inserted fragments were analyzed using ABI PRISM Dye Terminator Sequencing Ready Reaction Kit (manufactured by Perkin Elmer Co., Ltd.). As a result, the entire base sequence of the DNA fragment of about 1.0 kb which was expected to include an intended enzyme gene was determined. FIG. 1 shows the thus-determined base sequence. An amino acid sequence (SEQ ID NO: 1) predicted from the nucleotide sequence (SEQ ID NO: 2). The structural gene portion of the nucleotide sequence (SEQ ID NO: 9) is also shown under the corresponding nucleotide sequence in FIG. 1. The amino acid sequence (SEQ ID NO: 1) was compared with a partial amino acid sequences of lysyl endopeptidase digested peptide fragments of the purified CR enzyme (SEQ ID NO: 10, SEQ ID NO: 11, SEQ ID NO: 12, SEQ ID NO: 13, SEQ ID NO: 14, SEQ ID NO: 15). As a result, it was found that the partial amino acid sequences of the purified CR enzyme completely exists in the amino acid sequence and completely matches therewith (indicated as an underlined portion in the amino acid sequence in FIG. 1). Therefore, the DNA fragment was considered to include the CR enzyme gene.

Example 3

Preparation of Recombinant Plasmid Carrying CR Enzyme Gene

A double-stranded DNA having: an NdeI site added to an initiation codon portion of a structural gene of the CR enzyme; and a new termination codon (TAA) and an EcoRI site added immediately after a termination codon; and T substituted for G at sixth nucleotide from the 5' end of the gene in order to destroy an SalI site of the gene without an amino acid code modification, was obtained in the following manner. An N-terminus nucleotide primer having an NdeI site added to the initiation codon portion of the structural gene of the CR enzyme and T substituted for G at sixth nucleotide from the 5' end of the gene was synthesized based on the nucleotide sequence determined in Example 2. Further, a C-terminus nucleotide primer having the new termination codon (TAA) and an EcoRI site added immediately after the termination codon of the structural gene of the CR enzyme was synthesized based on the nucleotide sequence determined in Example 2. The nucleotide sequences of these two primers are represented by SEQ ID NOs. 5 and 6. Using the two synthetic DNA primers, a double-stranded DNA was amplified by PCR using the plasmid pUC-ES obtained in Example 2 as a template. The resultant DNA fragment was digested with NdeI and EcoRI, and inserted into NdeI and EcoRI sites downstream from the lac promoter of the plasmid pUCNT (W094/03613), to obtain recombinant plasmid pNTCR.

Example 4

Figure 2:
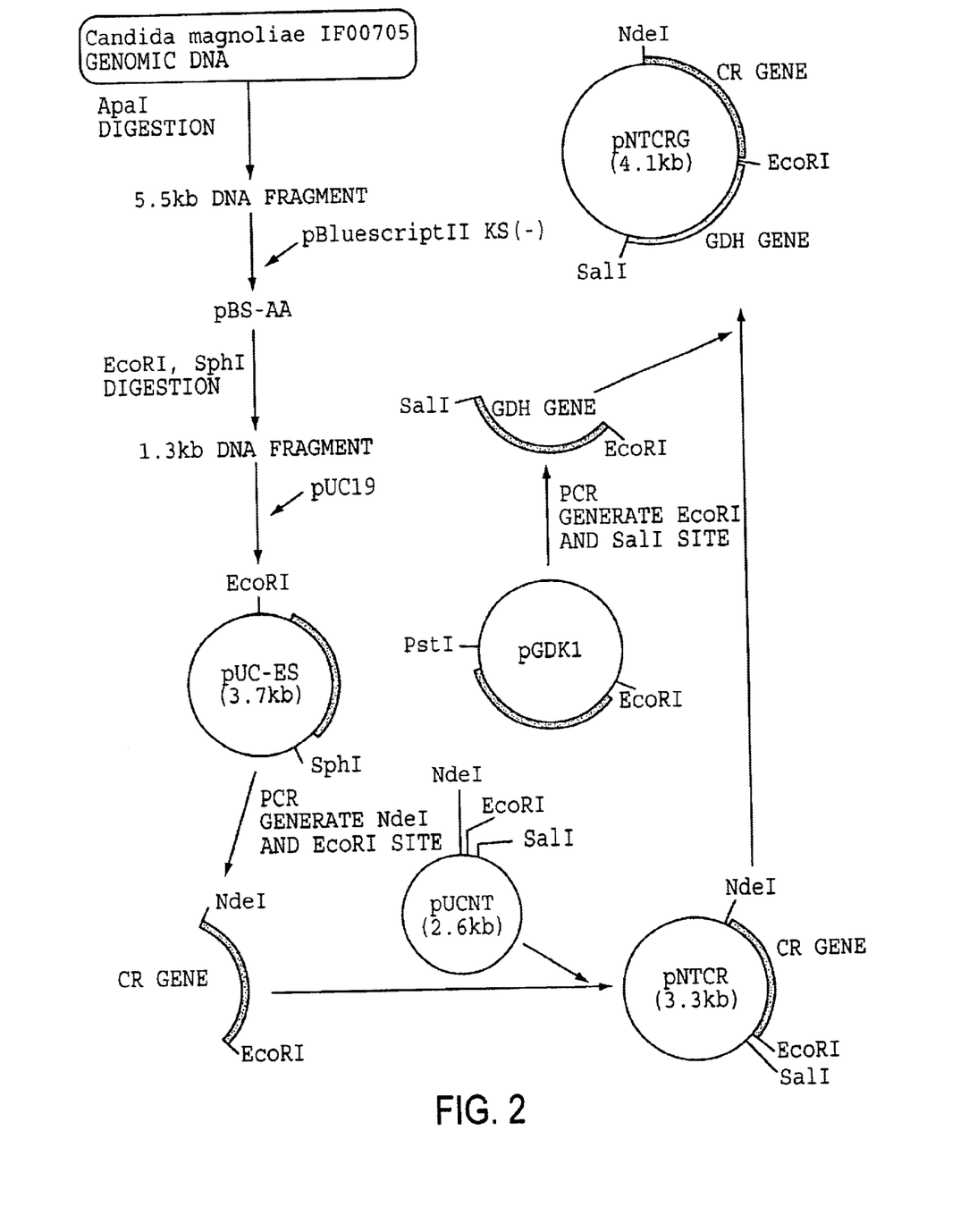
FIG. 2 is a diagram showing a method for producing the recombinant plasmid pNTCRG.

Production of Recombinant Plasmid Including Both CR Enzyme Gene and Glucose Dehydrogenase Gene A double-stranded DNA having: a Shine-Dalgarno sequence (9 nucleotides) of *E. coli* added 5 nucleotides upstream from the initiation codon of the glucose dehydrogenase (hereinafter referred to as GDH) gene derived from *Bacillus megaterium* IAM 1030; an EcoRI site added immediately therebefore; and an SalI site immediately after the termination codon was obtained in the following manner. Based on the nucleotide sequence information on the GDH gene, an N-terminus nucleotide primer having the Shine-Dalgarno sequence (9 nucleotides) of *E. coli* added 5 nucleotides upstream from the initiation codon of the structural gene of GDH and the EcoRI site added immediately therebefore, and a C-terminus nucleotide primer having the SalI site added immediately after the termination codon were synthesized with a conventional method. The nucleotide sequences of these two primers are represented by SEQ ID NOs. 7 and 8. Using the two synthetic DNA primers, a double-stranded DNA was synthesized by PCR using the plasmid pGDK 1(Eur. J. Biochem. 186, 389 (1989)) as a template. The resultant DNA fragment was digested with EcoRI and SalI, and inserted into EcoRI and SalI sites of pNTCR constructed in Example 3 (existing downstream from the CR enzyme gene) to obtain recombinant plasmid pNTCRG. The production method and structure of pNTCRG are shown in FIG. 2.

Example 5

Preparation of Recombinant *E. coli*

*E. coli* HB101 (manufactured by Takara Shuzo Co., Ltd.) was transformed using recombinant plasmid pNTCR obtained in Example 3 and the recombinant plasmid pNTCRG obtained in Example 4, to obtain recombinant *E. coli* HB101 (pNTCR) and HB101 (pNTCRG), respectively. The thus-obtained transformants, *E. coli* HB101 (pNTCR) and HB101 (pNTCRG), were deposited with the Ministry of International Trade and Industry, Agency of Industrial Science and Technology, National Institute of Bioscience and Human Technology (1-3, Higashi 1-chome, Tsukuba-shi, Ibaraki-ken, Japan) under the respective deposit numbers FERM BP-6897 and FERM BP-6898 on Sept. 28, 1999, pursuant to Budapest Treaty of the International Recognition of the Deposit of Microorganisms for the purposes of Patent Procedure.

Example 6

Expression of CR Enzyme in Recombinant *E. coli*

The recombinant *E. coli* HB101 (pNTCR) obtained in Example 5 was cultured in 2xYT medium containing 120 µg/ml of ampicillin, collected, suspended in a 100 mM phosphate buffer (pH 6.5), and subjected to ultrasonic treatment, to obtain a cell-free extract. The CR enzyme activity of the cell-free extract was measured in the following manner. That is, 5 mM tert-butyl (S)-6-chloro-5-hydroxy-3-oxohexanoate as a substrate, 0.333 mM NADPH as a coenzyme, and the enzyme were added to a 100 mM phosphate buffer (pH 6.5), and reduction in absorption at a wavelength of 340 nm was measured at 30° C. Under these reaction conditions, oxidation of 1 µmol NADPH into NADP in one minute was defined as one unit of enzyme activity. The thus-measured CR enzyme activity in the cell-free extract was represented as a specific activity and compared with that of a transformant holding only a vector plasmid. Also, the CR enzyme activity in a cell-free extract of *Candida magnoliae* IFO 0765 prepared in substantially the same manner as that described in Example 1 was compared. The results are shown in Table 1 below.

TABLE 1

Expression of CR enzyme in Recombinant *E. coli*

| Microorganism | CR enzyme specific activity (U/mg) |
| --- | --- |
| HB101 (pUCNT) | 0.12 |
| HB101 (pNTCR) | 3.76 |
| *Candida magnoliae* IFO 0705 | 0.11 |

As is seen from Table 1, *E. coli* HB101 (pNTCR) exhibited a definite increase in CR enzyme activity in comparison with *E. coli* HB101 (pUCNT) which was transformed using only a vector plasmid, and exhibited an activity about 34 times as large as that of *Candida magnoliae* IFO 0705.

Example 7

Simultaneous Expression of CR Enzyme and GDH in Recombinant *E. coli*

The GDH activity of a cell-free extract obtained by processing recombinant *E. coli* HB101 (pNTCRG) obtained in Example 5 in a manner as described in Example 6 was measured as follows. 0.1 M glucose as a substrate, 2 mM NADP as a coenzyme, and the enzyme were added to a 1 M Tris HCl buffer (pH 8.0), and an increase in absorption at a wavelength of 340 nm was measured at 25° C. Under these reaction conditions, reduction of 1 μmol NADP into NADPH in one minute was defined as one unit of enzyme activity. The CR enzyme activity was also measured as in Example 5. The thus-measured CR enzyme activity and GDH enzyme activity in the cell-free extract were represented as specific activities and compared with those of E. coli HB101 (pNTCR) and a transformant HB101 (pUCNT) using only a vector. The results are shown in Table 2 below.

TABLE 2

Simultaneous Expression of CR enzyme and GDH in Recombinant E. coli

| Microorganism | CR enzyme specific activity (U/mg) | GDH specific activity (U/mg) |
|---|---|---|
| HB101 (pUCNT) | 0.12 | <0.01 |
| HB101 (pNTCR) | 3.76 | <0.01 |
| HB101 (pNTCRG) | 2.16 | 87.8 |

As is seen from Table 2, E. coli HB101 (pNTCRG) exhibited a definite increase in CR enzyme activity and GDH activity in comparison with E. coli HB101(pUCNT) which was transformed using only a vector plasmid.

Example 8

Synthesis of tert-Butyl (3R,5S)-6-Chloro-3,5-dihydroxyhexanoate from tert-Butyl (S)-6-Chloro-5-hydroxy-3-oxohexanoate Using Recombinant E. coli Having CR Enzyme Gene Introduced Therein The recombinant E. coli HB101 (pNTCR) obtained in Example 5 was inoculated in 50 ml of 2xYT medium (Bacto tripton 1.6% (w/v), Bacto yeast extract 1.0% (w/v), NaCl 0.5% (w/v), pH 7.0) sterilized in a 500 ml Sakaguchi flask, and cultured with shaking at 37° C. for 16 hours. 680 units of GDH (manufactured by Amano Pharmaceutical Co., Ltd.), 5.0 g of glucose, 3.0 mg of NADP, and 4.5 g of tert-butyl (S)-6-chloro-5-hydroxy-3-oxohexanoate were added to 25 ml of the resultant culture. The culture was stirred at 30° C. for 40 hours while being adjusted at pH 6.5 with a 5 M aqueous sodium hydroxide solution. After the reaction, the reaction solution was subjected to extraction using ethyl acetate, and an extract after solvent removal was analyzed. As a result, it was found that tert-butyl (3R,5S)-6-chloro-3,5-dihydroxyhexanoate was produced at a yield of 96.9%. The diastereomer excess ratio of tert-butyl (3R,5S)-6-chloro-3,5-dihydroxyhexanoate was 98.2% de.

Quantification of tert-butyl (S)-6-chloro-5-hydroxy-3-oxohexanoate and tert-butyl (3R,5S)-6-chloro-3,5-dihydroxyhexanoate, and measurement of the diastereomer ratio of tert-butyl (3R,5S)-6-chloro-3,5-dihydroxyhexanoate were performed by high performance liquid chromatograhy (column: COSMOSIL 5CN-R (ID 4.6×250 mm) manufactured by Nacalai Tesque Co., Ltd., eluant: 1 mM phosphate solution/acetonitrile=5/1, flow rate: 0.7 ml/min, detection: 210 nm, column temperature: 30° C.).

Example 9

Synthesis of tert-Butyl (3R,5S)-6-Chloro-3,5-dihydroxyhexanoate from tert-Butyl (S)-6-Chloro-5-hydroxy-3-oxohexanoate Using Recombinant E. coli with CR Enzyme and GDH Expressed Simultaneously The recombinant E. coli HB101 (pNTCRG) obtained in Example 4 was inoculated in 100 ml of 2xYT medium (Bacto tripton 1.6% (w/v), Bacto yeast extract 1.0% (w/v), NaCl 0.5% (w/v), pH 7.0) sterilized in a 500 ml Sakaguchi flask, and cultured with shaking at 37° C. for 16 hours. 5.0 g of glucose, 1.5 mg of NADP, and 5.0 g of tert-butyl (S)-6-chloro-5-hydroxy-3-oxohexanoate were added to 25 ml of the resultant culture. The culture was stirred at 30° C. for 24 hours while being adjusted to pH 6.5 with a 5 M aqueous sodium hydroxide solution. After the reaction, the reaction solution was subjected to extraction using ethyl acetate, and an extract after solvent removal was analyzed. As a result, it was found that tert-butyl (3R,5S)-6-chloro-3,5-dihydroxyhexanoate was produced at a yield of 97.2%. The diastereomer excess ratio of tert-butyl (3R,5S)-6-chloro-3,5-dihydroxyhexanoate was 98.5% de.

INDUSTRIAL APPLICABILITY

It is possible to clone genes of polypeptides having the enzyme activity to asymmetrically reduce tert-butyl (S)-6-chloro-5-hydroxy-3-oxohexanoate to tert-butyl (3R,5S)-6-chloro-3,5-dihydroxyhexanoate, and obtain transformants having a high level of capability to produce the polypeptides by analyzing the nucleotide sequences of the genes. Further, it is possible to obtain transformants capable of producing the polypeptides and glucose dehydrogenase simultaneously to a large extent. Furthermore, it is possible to synthesize tert-butyl (3R,5S)-6-chloro-3,5-dihydroxyhexanoate from tert-butyl (S)-6-chloro-5-hydroxy-3-oxohexanoate using the transformants.

What is claimed is:

1. An isolated polypeptide having an enzyme activity to asymmetrically reduce tert-butyl (S)-6-chloro-5-hydroxy-3-oxohexanoate to tert-butyl (3R, 5S)-6-chloro-3,5-dihydroxyhexanoate, wherein the polypeptide comprises the amino acid sequence of SEQ ID NO: 1.

2. An isolated polypeptide according to claim 1, wherein the peptide is derived from a microorganism belonging to the genus Candida.

3. An isolated polynucleotide encoding a polypeptide having an enzyme activity to asymmetrically reduce tert-butyl (S)-6-chloro-5-hydroxy-3-oxohexanoate to tert-butyl (3R,5S)-6-chloro-3,5-dihydroxyhexanoate, wherein the polynucleotide hybridizes to a nucleotide sequence represented by SEQ ID NO: 2 under stringent conditions; whereby the stringent conditions comprise hybridization conditions having about 0.7 to about 1.0M sodium chloride concentration at about 65° C. and wash conditions having about 0.015M sodium chloride concentration to about 0.3M sodium chloride concentration at about 65° C.

4. An expression vector comprising a polynucleotide encoding a polypeptide having an enzyme activity to asymmetrically reduce tert-butyl (S)-6-chloro-5-hydroxy-3-oxohexanoate to tert-butyl (3R,5S)-6-chloro-3,5-dihydroxyhexanoate, wherein the polynucleotide hybridizes to a nucleotide sequence represented by SEQ ID NO: 2 under stringent conditions; whereby the stringent conditions comprise hybridization conditions having about 0.7 to about 1.0M sodium chloride concentration at about 65° C. and wash conditions having about 0.015M sodium chloride concentration to about 0.3M sodium chloride concentration at about 65° C.

5. The expression vector according to claim 4, wherein the polypeptide has the sequence represented by SEQ ID NO: 1.

6. The expression vector according to claim 4, further encoding an enzyme capable of reducing NADP or NAD.

7. The expression vector according to claim 6, wherein the enzyme has glucose dehydrogenase activity.

8. The expression vector according to claim 7, wherein the enzyme having glucose dehydrogenase activity is derived from *Bacillus megaterium*.

9. The expression vector according to claim 5, further encoding an enzyme having glucose dehydrogenase activity derived from *Bacillus megaterium*.

10. A transformed host cell comprising the expression vector of claim 4.

11. The transformed host cell of claim 10, wherein the transformant is *E.coli* HB101 (pNTCR).

12. The transformed host cell of claim 10, wherein the transformant is *E.coli* HB101 (pNTCRG).

13. An isolated polypeptide having an enzyme activity to asymmetrically reduce tert-butyl (S)-6-chloro-5-hydroxy-3-oxohexanoate to tert-butyl (3R,5S)-6-chloro-3,5-dihydroxyhexanoate, wherein the polypeptide is encoded by a polynucleotide that hybridizes to a nucleotide sequence represented by SEQ ID NO: 2 under stringent conditions; whereby the stringent conditions comprise hybridization conditions having about 0.7 to about 1.0M sodium chloride concentration at about 65° C. and wash conditions having about 0.015M sodium chloride concentration to about 0.3M sodium chloride concentration at about 65° C.

14. A method for producing a tert-butyl (3R,5S)-6-chloro-3,5-dihydroxyhexanoate comprising the steps:

a) reacting a host cell, or cell lysate thereof, said cell comprising an expression vector further comprising a polynucleotide encoding a polypeptide having an enzyme activity to asymmetrically reduce tert-butyl (S)-6-chloro-5-hydroxy-3-oxohexanoate to tert-butyl (3R,5S)-6-chloro-3,5-dihydroxyhexanoate wherein the polynucleotide hybridizes to a nucleotide sequence represented by SEQ ID NO: 2 under stringent conditions, whereby the stringent conditions comprise hybridization conditions having about 0.7 to about 1.0 M sodium chloride concentration at about 65° C. and wash conditions having about 0.015 M sodium chloride concentration to about 0.3 M sodium chloride concentration at about 65° C., with tert-butyl (S)-6-chloro-5-hydroxy-3-oxohexanoate; and b) obtaining said tert-butyl (3R,5S)-6-chloro-3,5-dihydroxyhexanoate.

15. A method according to claim 14, wherein the reacting step is carried out in the presence of an enzyme capable of reducing NADP or NAD.

* * * * *

SEQUENCE LISTING

```
<160> NUMBER OF SEQ ID NOS: 15

<210> SEQ ID NO 1
<211> LENGTH: 241
<212> TYPE: PRT
<213> ORGANISM: Candida magnoliae IFO 0705

<400> SEQUENCE: 1

Met Ser Thr Pro Leu Asn Ala Leu Val Thr Gly Ala Ser Arg Gly Ile
 1               5                   10                  15
```

```
Gly Ala Ala Thr Ala Ile Lys Leu Ala Glu Asn Gly Tyr Ser Val Thr
            20                  25                  30

Leu Ala Ala Arg Asn Val Ala Lys Leu Asn Gly Val Lys Gly Lys Leu
            35                  40                  45

Pro Val Val Lys Asp Gly Gly Lys His His Ile Trp Glu Leu Asp Leu
 50                  55                  60

Ala Ser Val Glu Ala Ala Ser Ser Phe Lys Gly Ala Pro Leu Pro Ala
 65                  70                  75                  80

Ser Asp Tyr Asp Leu Phe Val Ser Asn Ala Gly Ile Ala Gly Phe Thr
                 85                  90                  95

Pro Thr Ala Asp Gly Thr Asp Lys Asp Phe Leu Asn Ile Leu Thr Val
            100                 105                 110

Asn Leu Ser Ser Pro Ile Ala Leu Thr Lys Ala Leu Leu Lys Gly Val
            115                 120                 125

Ser Glu Arg Ser Asn Glu Lys Pro Phe His Ile Phe Leu Ser Ser
            130                 135                 140

Ala Ala Ala Leu His Gly Val Pro Gly Thr Ala Val Tyr Ser Ala Ser
145                 150                 155                 160

Lys Ala Gly Leu Asp Gly Phe Val Arg Ser Leu Ala Arg Gly Val Gly
                165                 170                 175

Pro Lys Gly Ile His Val Asn Val Ile His Pro Gly Trp Thr Lys Thr
                180                 185                 190

Asp Met Thr Asp Gly Ile Asp Asp Pro Asn Asp Thr Pro Ile Lys Gly
            195                 200                 205

Trp Ile Gly Pro Glu Ala Ile Ala Asp Ala Val Val Phe Leu Ala Lys
210                 215                 220

Ser Lys Asn Ile Thr Gly Thr Asn Ile Val Val Asp Asn Gly Leu Leu
225                 230                 235                 240

Ala

<210> SEQ ID NO 2
<211> LENGTH: 726
<212> TYPE: DNA
<213> ORGANISM: Candida magnoliae IFO 0705

<400> SEQUENCE: 2
atgtcgactc cgttgaatgc tctcgtaact ggcgctagcc gcggcattgg cgctgctact    60
gccattaagc tcgccgagaa tggatacagt gtgacgctgg ctgcgcgtaa tgtcgcgaag   120
ctgaacgaag tgaaggagaa gctgcctgtg gtcaaggacg gccagaagca ccacatctgg   180
gagctcgatc ttgcgagcgt tgaggctgca tcgtccttca agggcgcgcc tttaccggct   240
agcgactacg atctgttcgt ttcgaatgct ggcattgcgc agttcacgcc aacggcggac   300
caaaccgaca aggacttcct gaacattctc accgtgaacc tctcctcccc cattgcgctc   360
acgaaggccc tactgaaggg cgtctccgag aggtcgaacg agaagccgtt ccatattatc   420
ttcctctcgt ccgctgcagc cctgcacgga gtccctcaga ctgcagtcta cagtgcttcg   480 aaggcgggc ttgacggttt cgtgcgctct cttgctcgcg aggtgggtcc gaagggcatt   540
catgtgaacg ttattcatcc tggttggacg aagactgaca tgacggatgg tattgacgac   600
cccaatgata ctcctatcaa gggctggatc cagcctgagg cgattgctga tgcggttgtg   660
ttcctggcaa agtcgaagaa catcacaggc actaatatcg tggtggacaa tggcttgctc   720
gcttga                                                             726
```

<210> SEQ ID NO 3
<211> LENGTH: 20
<212> TYPE: DNA
<213> ORGANISM: Artificial Sequence
<220> FEATURE:
<223> OTHER INFORMATION: Primer
<221> NAME/KEY: misc_feature
<222> LOCATION: 3
<223> OTHER INFORMATION: n = A,T,C or G
<221> NAME/KEY: misc_feature
<222> LOCATION: 3
<223> OTHER INFORMATION: n = A,T,C or G

<400> SEQUENCE: 3
atngcytcrg gytgdatcca                                               20

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
gcgcatatgt ctactccgtt gaatgctctc gta                                33

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5
ggcgaattct tatcaagcga gcaagccatt gtc                                33

<210> SEQ ID NO 6
<211> LENGTH: 20
<212> TYPE: DNA
<213> ORGANISM: Artificial Sequence
<220> FEATURE:
<223> OTHER INFORMATION: Primer
<221> NAME/KEY: misc_feature
<222> LOCATION: 3, 6
<223> OTHER INFORMATION: n = A,T,C or G
<221> NAME/KEY: misc_feature
<222> LOCATION: 3, 6
<223> OTHER INFORMATION: n = A,T,C or G

<400> SEQUENCE: 6
acngcngayc aracygayaa                                               20

<210> SEQ ID NO 7
<211> LENGTH: 43
<212> TYPE: DNA
<213> ORGANISM: Artificial Sequence
<220> FEATURE:
<223> OTHER INFORMATION: Primer

<400> SEQUENCE: 7
gccaaattct aaggaggtta acaatgtata aagatttaga agg                     43

<210> SEQ ID NO 8
<211> LENGTH: 28
<212> TYPE: DNA
<213> ORGANISM: Artificial Sequence
<220> FEATURE:
<223> OTHER INFORMATION: Primer -continued

```
<400> SEQUENCE: 8
gcggtcgact tatccgcgtc ctgcttgg                                              28

<210> SEQ ID NO 9
<211> LENGTH: 1003
<212> TYPE: DNA
<213> ORGANISM: Candida magnoliae IFO 0705
<220> FEATURE:
<221> NAME/KEY: CDS
<222> LOCATION: (146)...(871)

<400> SEQUENCE: 9
gcatgcacgc tacgaagtgt gcttacagat gtcacgtaag tgtgcatgtg cgttgcgtgt           60
gcgttgcgtg tgtgttgtgg gaatataaaa gggcgcagtt gacttgactc gagactgtgc         120
actaacctac accaaagcta caaag atg tcg act ccg ttg aat gct ctc gta           172
                              Met Ser Thr Pro Leu Asn Ala Leu Val
                                1               5 act ggc gct agc cgc ggc att ggc gct gct act gcc att aat ctc gcc           220
Thr Gly Ala Ser Arg Gly Ile Gly Ala Ala Thr Ala Ile Asn Leu Ala
 10              15                  20                  25 gag aat gga tac agt gtg acg ctg gct gcg cgt aat gtc gcg aag ctg           268
Glu Asn Gly Tyr Ser Val Thr Leu Ala Ala Arg Asn Val Ala Lys Leu
                 30                  35                  40 aac gaa gtg aag gag aag ctg cct gtg gtc aag gac ggc cag aag cac           316
Asn Glu Val Lys Glu Lys Leu Pro Val Val Lys Asp Gly Gln Lys His
             45                  50                  55 cac atc tgg gag ctc gat ctt gcg agc gtt gat tct gca tcg tcc ttc           364
His Ile Trp Glu Leu Asp Leu Ala Ser Val Asp Ser Ala Ser Ser Phe
         60                  65                  70 aag ggc gcg cct tta ccg gct agc gac tac gat ctg ttc gtt tcg aat           412
Lys Gly Ala Pro Leu Pro Ala Ser Asp Tyr Asp Leu Phe Val Ser Asn
     75                  80                  85 gct ggc att gcg cag ttc acg cca acg gcg gac caa acc gac aag gac           460
Ala Gly Ile Ala Gln Phe Thr Pro Thr Ala Asp Gln Thr Asp Lys Asp
 90                  95                 100                 105 ttc ctg aac att ctc acc gtg aac ctc tcc tcc ccc att gcg ctc acg           508
Phe Leu Asn Ile Leu Thr Val Asn Leu Ser Ser Pro Ile Ala Leu Thr
                110                 115                 120 aag gcc cta ctg aag ggc gtc tcc gag agg tcg aac gag aag ccg ttc           556
Lys Ala Leu Leu Lys Gly Val Ser Glu Arg Ser Asn Glu Lys Pro Phe
            125                 130                 135 cat att atc ttc ctc tcg tcc gct gca gcc ctg cac gga gtc cct cag           604
His Ile Ile Phe Leu Ser Ser Ala Ala Ala Leu His Gly Val Pro Gln
        140                 145                 150 act gca gtc tac agt gct tcg aag gcg ggg ctt gac ggt ttc gtg cgc           652
Thr Ala Val Tyr Ser Ala Ser Lys Ala Gly Leu Asp Gly Phe Val Arg
    155                 160                 165 tct ctt gct cgc gag gtg ggt tcg aag ggc att cat gtg aac gtt att           700
Ser Leu Ala Arg Glu Val Gly Ser Lys Gly Ile His Val Asn Val Ile
170                 175                 180                 185 cat cct ggt tgg acg aag act gac atg acg gat ggt att gac gac ccc           748
His Pro Gly Trp Thr Lys Thr Asp Met Thr Asp Gly Ile Asp Asp Pro
                190                 195                 200 aat gat act cct atc aag ggc tgg atc cag cct gag gcg att gct gat           796
Asn Asp Thr Pro Ile Lys Gly Trp Ile Gln Pro Glu Ala Ile Ala Asp
            205                 210                 215 gcg gtt gtg ttc ctg gca aag tcg aag aac atc aca ggc act aat atc           844
Ala Val Val Phe Leu Ala Lys Ser Lys Asn Ile Thr Gly Thr Asn Ile
        220                 225                 230
```

-continued

```
gtg gtg gac aat ggc ttg ctc gct tga gtagatagaa cggttttacg      891
Val Val Asp Asn Gly Leu Leu Ala *
    235                 240 caatgttgtt attacactta tcggcaagga aactgctttt atggagcatg gcctagtgta   951
ttgaaactcc aaaaattaat tagagcatac aacacatggc accaccgaat tc          1003
```

<210> SEQ ID NO 10
<211> LENGTH: 18
<212> TYPE: PRT
<213> ORGANISM: Candida magnoliae IFO 0705

<400> SEQUENCE: 10

```
His His Ile Trp Glu Leu Asp Leu Ala Ser Val Asp Ser Ala Ser Ser
 1               5                  10                  15

Phe Lys
```

<210> SEQ ID NO 11
<211> LENGTH: 30
<212> TYPE: PRT
<213> ORGANISM: Candida magnoliae IFO 0705

<400> SEQUENCE: 11

```
Gly Ala Pro Leu Pro Ala Ser Asp Tyr Asp Leu Phe Val Ser Asn Ala
 1               5                  10                  15

Gly Ile Ala Gln Phe Thr Pro Thr Ala Asp Gln Thr Asp Lys
             20                  25                  30
```

<210> SEQ ID NO 12
<211> LENGTH: 18
<212> TYPE: PRT
<213> ORGANISM: Candida magnoliae IFO 0705

<400> SEQUENCE: 12

```
Asp Phe Leu Asn Ile Leu Thr Val Asn Leu Ser Ser Pro Ile Ala Leu
 1               5                  10                  15

Thr Lys
```

<210> SEQ ID NO 13
<211> LENGTH: 52
<212> TYPE: PRT
<213> ORGANISM: Candida magnoliae IFO 0705

<400> SEQUENCE: 13

```
Gly Val Ser Glu Arg Ser Asn Glu Lys Pro Phe His Ile Ile Phe Leu
 1               5                  10                  15

Ser Ser Ala Ala Ala Leu His Gly Val Pro Gln Thr Ala Val Tyr Ser
             20                  25                  30

Ala Ser Lys Ala Gly Leu Asp Gly Phe Val Arg Ser Leu Ala Arg Glu
         35                  40                  45

Val Gly Ser Lys
     50
```

<210> SEQ ID NO 14
<211> LENGTH: 20
<212> TYPE: PRT
<213> ORGANISM: Candida magnoliae IFO 0705

<400> SEQUENCE: 14

```
Gly Ile His Val Asn Val Ile His Pro Gly Trp Thr Lys Thr Asp Met
 1               5                  10                  15
```

-continued

```
Thr Asp Gly Ile
            20

<210> SEQ ID NO 15
<211> LENGTH: 17
<212> TYPE: PRT
<213> ORGANISM: Candida magnoliae IFO 0705

<400> SEQUENCE: 15

Gly Trp Ile Gln Pro Glu Ala Ile Ala Asp Ala Val Val Phe Leu Ala
1               5                   10                  15

Lys
```